(12) United States Patent
Goglin et al.

(10) Patent No.: US 6,490,531 B1
(45) Date of Patent: Dec. 3, 2002

(54) OPTIMIZED METHOD FOR DETERMINING PHYSICAL PARAMETERS OF A SAMPLE SUBJECTED TO CENTRIFUGATION

(75) Inventors: Elodie Goglin, Bignicourt (FR); Marc Fleury, Domalne St François d'Asslse (FR); Patrick Egermann, Rueil Malmalson (FR)

(73) Assignee: Institut Francais du Petrole, Rueil-Malmaison cedex (FR)

( * ) Notice: Subject to any disclaimer, the term of this patent is extended or adjusted under 35 U.S.C. 154(b) by 10 days.

(21) Appl. No.: 09/666,568

(22) Filed: Sep. 20, 2000

(30) Foreign Application Priority Data

Sep. 21, 1999 (FR) ............................................. 99 12266

(51) Int. Cl.[7] ............................................. G01N 15/08
(52) U.S. Cl. ..................... 702/25; 702/45; 702/146; 73/152.06
(58) Field of Search ................. 73/38, 152.06, 73/597; 702/25, 45, 146

(56) References Cited

U.S. PATENT DOCUMENTS

| | | | |
|---|---|---|---|
| 4,740,077 A | 4/1988 | Goodwill | 356/23 |
| 5,373,727 A | 12/1994 | Heller et al. | 73/38 |
| 5,463,894 A | 11/1995 | Fleury et al. | 73/38 |
| 5,679,885 A | 10/1997 | Lenormand et al. | 73/38 |

FOREIGN PATENT DOCUMENTS

| | | | |
|---|---|---|---|
| EP | 0586001 | 3/1994 | G01N/15/08 |

*Primary Examiner*—Kamini Shah
(74) *Attorney, Agent, or Firm*—Antonelli, Terry, Stout & Kraus, LLP

(57) ABSTRACT

A method for faster determination of physical parameters (capillary pressure curves and relative permeabilities for example) of a geologic sample initially saturated with a first fluid placed in a vessel and subjected to centrifugation in the presence of a second fluid. The equilibrium saturations are determined before complete stabilization is reached through analytic modelling involving exponential functions, best adjusting to an effective production curve, for each speed stage. A database, obtained by means of various simulations, is used to obtain the relative permeability curves corresponding to the centrifuged sample. The method can be applied for measurement of petrophysical characteristics.

18 Claims, 11 Drawing Sheets

| Time (h) | 101.6 | 122.04 | 123 | 124.56 | 150.24 |
|---|---|---|---|---|---|
| $T_2$ ($h^{-1}$) | | 0.21752 | 0.24931 | 0.25233 | 0.24255 |
| Sfinal | | 0.01064 | 0.01074 | 0.01080 | 0.01084 |
| Error on $T_2$ (%) | | 10.44248 | 2.64543 | 3.88978 | 0.13713 |
| Error on Sfinal (%) | | 1.78773 | 0.92107 | 0.40525 | 0.00972 |

FIG.7

| Time (h) | 3.07806 | 3.57805556 | 5.15722 | 5.84111 |
|---|---|---|---|---|
| $T_2$ ($h^{-1}$) | 1.45842 | 1.81289 | 1.55651 | 1.60005 |
| Sfinal | 0.97379 | 1.00749 | 0.99701 | 1.00092 |
| Error on $T_2$ (%) | 8.85142 | 13.3027 | 2.72111 | 0.00000 |
| Error on Sfinal (%) | 2.71030 | 0.65730 | 0.39043 | 0.00000 |

|   |  | Conventional Drainage | | Fast Drainage | | Error (%) | |
|---|---|---|---|---|---|---|---|
|   |   | 1 | 2 | 1 | 2 | 1 | 2 |
| $V_1$ | $S_{final}$ | 0.345 | 0.424 | 0.331 | 0.401 | 4.03 | 5.51 |
|  | Duration | 45 | | 10 | | Gain 78 % | |
|  | Accuracy | 2.586E-05 | 1.711E-05 | 1.404E-06 | 1.761E-06 | | |
| $V_2$ | $S_{final}$ | 0.502 | 0.632 | 0.508 | 0.636 | 1.10 | 0.64 |
|  | Duration | 25 | | 15 | | Gain 40 % | |
|  | Accuracy | 5.193E-06 | 3.481E-06 | 1.341E-05 | 1.403E-05 | | |
| $V_3$ | $S_{final}$ | 0.795 | 0.908 | 0.827 | 0.897 | 3.95 | 1.23 |
|  | Duration | 25 | | 6 | | Gain 75 % | |
|  | Accuracy | 1.535E-05 | 7.565E-06 | 1.628E-06 | 3.767E-07 | | |

OPTIMIZED METHOD FOR DETERMINING PHYSICAL PARAMETERS OF A SAMPLE SUBJECTED TO CENTRIFUGATION

BACKGROUND OF THE INVENTION

1. Field of the Invention

The present invention relates to a modelling method allowing more rapid obtaining of physical parameters of a geologic sample from experimental results obtained by subjecting the sample to centrifugation.

2. Description of the Prior Art

A well-known method for rapidly determining both the capillary pressure curves and the relative permeability curves of a porous rock sample initially saturated with a first fluid essentially consists in subjecting the sample to centrifugation in order to displace the fluid in place by means of another fluid.

Centrifugation devices such as those described in U.S. Pat. No. 5,463,894, French Patent 2,763,690, and U.S. Pat. No. 6,185,985 filed by the Assignee are for example used.

The sample initially saturated with a liquid A (brine for example) is placed in an elongate vessel or cup containing another fluid B of different density (oil for example). The vessel is fastened to the end of a rotating arm and a centrifugal force is applied thereto so as to study the displacements of the fluids in the sample during at least two distinct stages. During a first drainage stage, the assembly is subjected to a centrifugal force exerted along the length of the vessel so as to exert thereon an expulsion force which tends to cause part of first fluid A to flow out. Simultaneously, part of fluid A penetrates the sample. The two fluids move in the sample to a position of equilibrium where the force due to the capillary pressure in the pores makes up for the centrifugal force exerted. A measuring sonde is placed in the vessel, on the side of the sample. The sonde can be a capacitive type sonde for example, and it can comprise a metal rod insulated by means of a ceramic sheath. The capacitance between the rod and the conducting fluid (brine), which is proportional to the height immersed, is measured. With this system, the measuring accuracy is 1.5% of the pore volume. The sonde detects the position of the interface between the two liquids in the vessel and transmits the measurement signals to a signal acquisition and control device comprising hydraulic liquid circulation means and an acquisition device.

Figure 11:
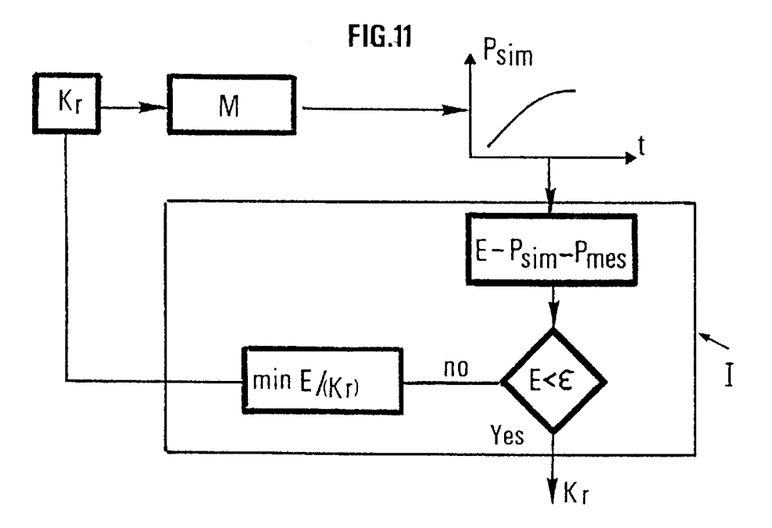

The various points of the capillary pressure curve (Pc) are obtained from measurement of the mean saturation of the sample at equilibrium for given rotating speeds. Determination of the relative permeability curves (Kr) is achieved by means of the saturation variation with time between two (transient) speed stages. None of these curves is obtained directly; the first one must be calculated and the second one requires a numerical flow simulator comprising (FIG. 11) a simulation module which reproduces the effects of the experiment by means of a numerical model, and an inversion module allowing to determine capillary pressure and relative permeability curves by iterative adjustment of an initial numerical model to the experimental results.

An example of a well-known flow simulator is the ACEX flow simulator based on Darcy's generalized equations, which is described in:

Chardaire-Rivière, C.; 1992, Improving the Centrifuge Technique by Measuring Local Saturations; SPE 24882.

Although the centrifugation technique is widely used in the petroleum industry, because of its relative rapidity in relation to other existing methods, some implementation difficulties remain concerning determination of the capillary pressure curve as well as the relative permeability curves.

For a given speed stage, the transient state is difficult to determine since a very slow production stabilization is observed. Search for this equilibrium leads to long-lasting operations spread over several weeks, whose implementation presents practical difficulties, considering especially the often high rotating speed of the centrifuge. Furthermore, the time required therefore is even longer if one tries to increase the pore volume of the sample (by increasing the length thereof) in order to improve the saturation measuring accuracy.

Inversion, i.e. adjustment of a numerical model to experimental results, is difficult to achieve because the information relating to the relative permeabilities is concentrated on the transient part of the production curve, i.e. in a narrow range of experimental values. The acceleration applied to the centrifuge has a preponderant effect on the form of this transient part, notably its duration. Parallel determination of the capillary pressure curve leads to applying several constant speed stages rather than a long acceleration, which reduces the transient curves.

SUMMARY OF THE INVENTION

The modelling method according to the invention allows obtaining, with a considerable gain in time, the values of physical parameters of a geologic sample initially saturated with a first fluid placed in a vessel and subjected to centrifugation in the presence of a second fluid.

It comprises measuring the amount of fluids displaced by centrifugation and establishing saturation curves, at fixed time intervals, and comprises, for each rotating speed stage, modelling of a saturation curve best adjusting, at each time interval, to the curve portion already obtained and corresponding to the various previous measurements, the value of the saturation at equilibrium being deduced from characteristics of the modelled curve.

For each speed stage, an exponential type saturation curve is modelled by adjusting parameters, one of these parameters corresponding to the value of the saturation at equilibrium. The saturation curve is modelled for example by means of a sum of exponential functions depending on the adjustment parameters.

Centrifugation speeds allowing obtaining an even distribution of points on each saturation curve are preferably selected.

According to an embodiment, the method further comprises:

using a flow simulator for modelling a relation between the relative permeability values in relation to the two fluids for a sample of determined dimensions and permeability, and the saturation values in relation to these fluids according to various coefficients, and establishing a database connecting parameters intended for adjustment to the coefficients, for several saturation values in relation to at least one of the fluids, and determining relative permeabilities of the sample subjected to centrifugation with reference to correspondence values extracted from the database.

The method has applications in the field of petrophysics where knowledge of parameters such as the capillary pressure, the relative permeability curves of porous rocks, allow reservoir engineers to characterize the flow conditions of hydrocarbons in a reservoir, to make production predictions and to elaborate development strategies.

BRIEF DESCRIPTION OF THE DRAWINGS

Other features and advantages of the method according to the invention will be clear from reading the description hereafter of a non limitative example, with reference to the accompanying drawings wherein.

DETAILED DESCRIPTION OF THE PREFERRED EMBODIMENTS

A centrifugation device as described hereafter is used for implementing the method.

The device comprises (FIG. 1) an elongate vessel or cup 13 intended for a sample. A capacitive type level-detecting sonde (not shown) is arranged in a tubular lateral chamber parallel to the direction of elongation of the sample and of the vessel. Any variation in the level of the conducting fluid in the vessel leads to a capacitance variation of the sonde. Centrifuge 11 comprises a tank 9, an electric motor 10 whose shaft drives a hub 11 in rotation. Two identical arms 12 are mounted in opposition on hub 11. Two vessels or cups 13 and 14 are mounted swivelling at the ends of arms 12 so as to spontaneously line up along the direction of the centrifugal force applied, and they balance each other in rotation. A porous rock sample to be measured, initially saturated with an electrically conducting fluid A, such as brine for example, is placed in vessel 13. Vessel 13 is initially filled with an electrically insulating other fluid B such as oil.

Figure 1:
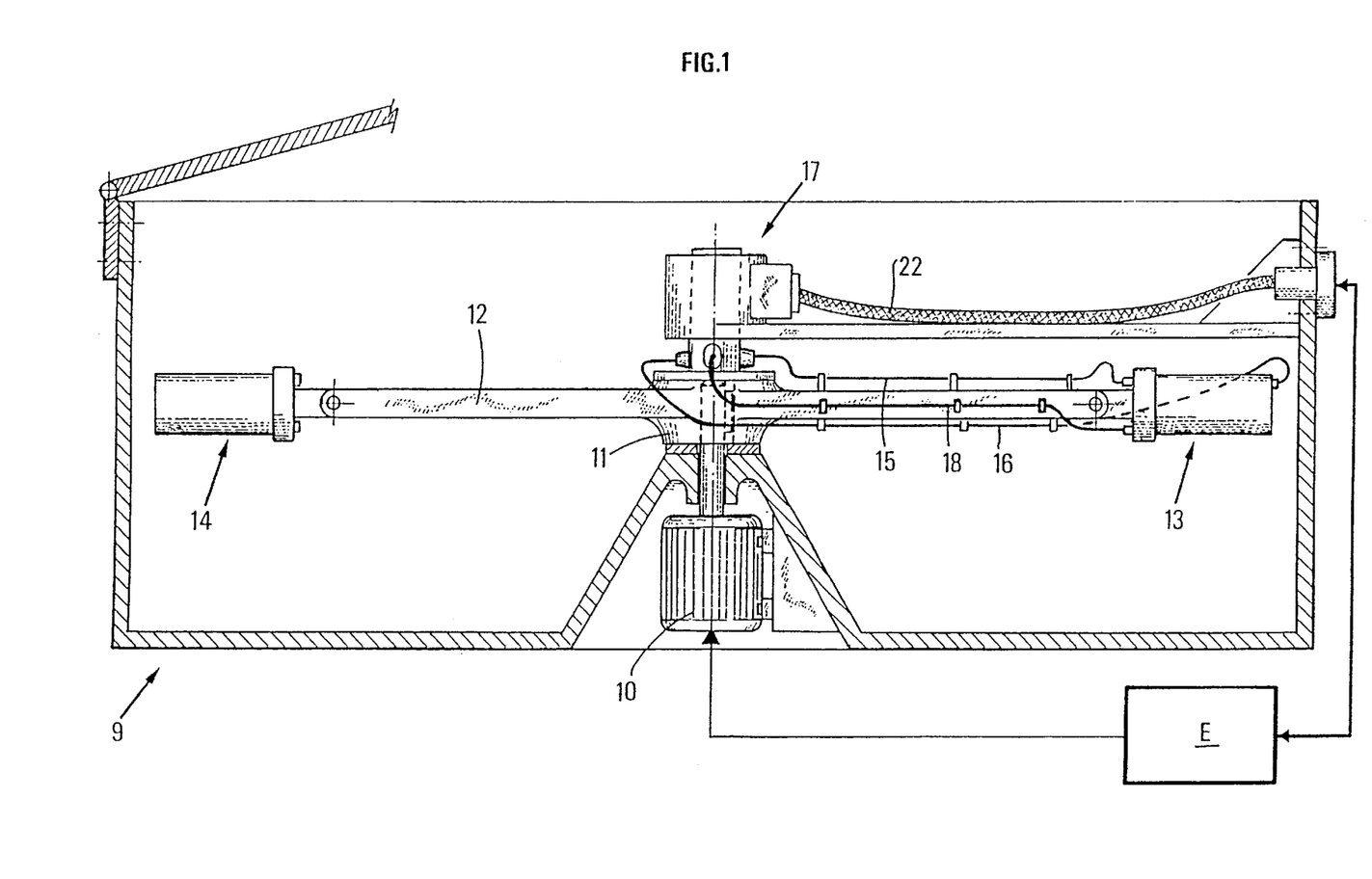
FIG. 1 shows a centrifugation device allowing the method to be implemented.

Two lines 15 and 16, fastened along one of arms 12, connect vessel 13 to a rotary electro-hydraulic connector 17 carried by hub 11. First line 15 is used for injecting oil into vessel 13. The second line 16, is used for collecting the brine drained out of the sample by the rotation. A cable 18 connects the measuring sonde to rotary connector 17. By means of connector 17, the conductors of cable 18 are electrically connected to another cable 21. These two lines and the cable 18 form a linking element 22 between vessel 13 and an external assembly E suited to collect the signals coming from the sonde, to process the acquired data, to control fluid transfers and to actuate driving motor 10.

The method comprises first selecting a certain number of rotating speed stages selected to obtain well-distributed points on the saturation curve. The operator can select them by referring to values obtained with previous tests for samples of the same type. Failing that, the operator can also quickly carry out a test on a sample by means of a Purcell type method which is well-known, so as to establish a corresponding capillary pressure curve and, according to the form thereof, to estimate the suitable speed stages.

The fast access to the saturation values obtained with the method is based on analytic modelling of the fluid production stages of the sample subjected to centrifugation. An exponential type modelling equation is used therefore.

It has been found that most production curves can be modelled by the following equation:

$$S(t) = S_{eq}[1-(P \cdot e^{-t/R_1} + (1-P) \cdot e^{-t/T_2})] + S_{ini}$$

where $S_{eq}$ is the saturation at equilibrium, $S_{ini}$, the initial saturation of the previous speed stage, t the time, P a weighting factor, and $T_1$ and $T_2$ are time constants.

The lowest time constant T1 describes the transient part C1 of the saturation curve (FIG.2), i.e. the dynamic effects. The highest time constant T2 describes stabilization zone C2, i.e. capillary effects.

Figure 2:
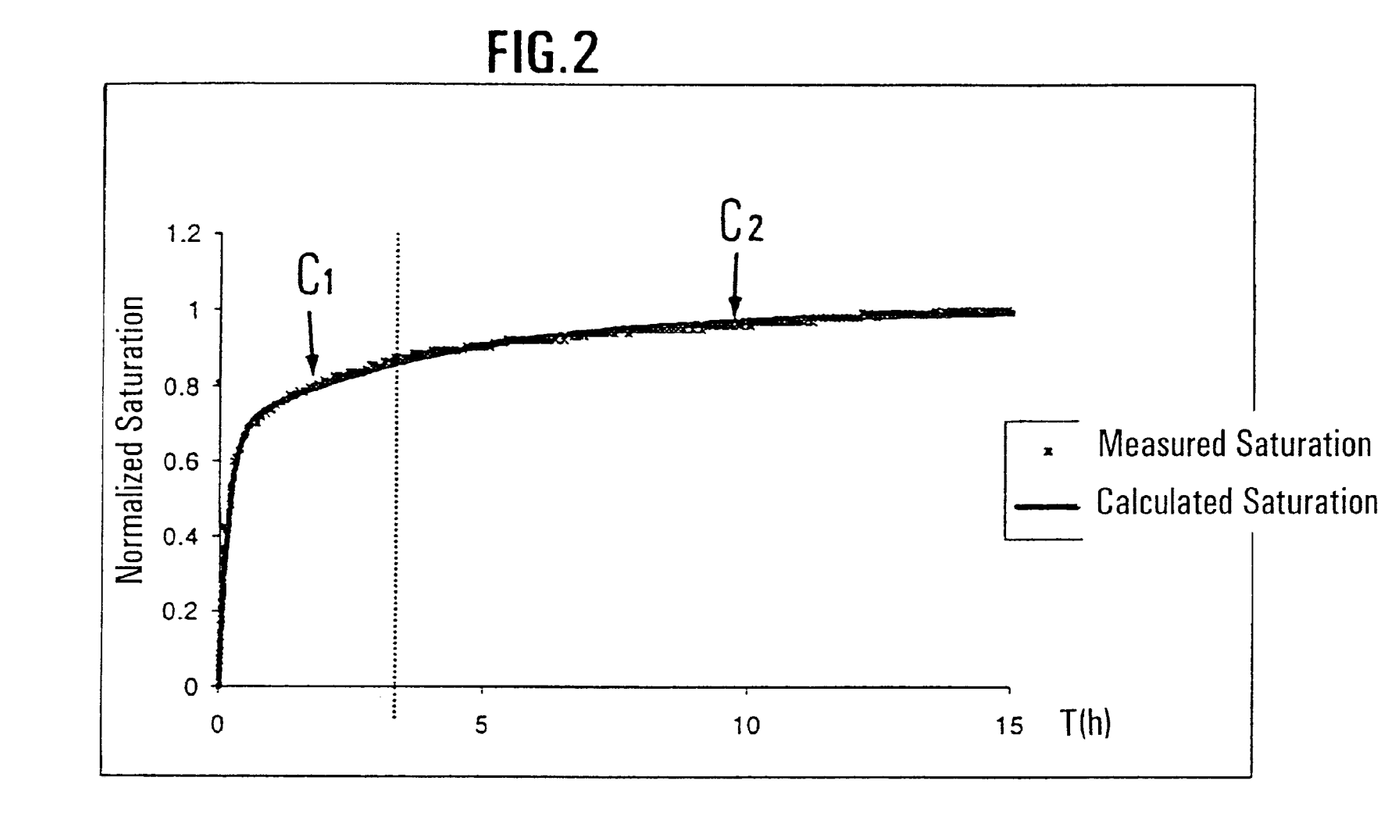
FIG. 2 shows an example of adjustment of a modelling curve to an experimental production curve.

In order to estimate the saturation at equilibrium, long before the stage where its variations actually become lower than the measuring accuracy, coefficients T1 and T2 are sought which, applied in the equation above, generate a saturation curve that adjusts to the part of the production curve that is already known.

Figure 3:
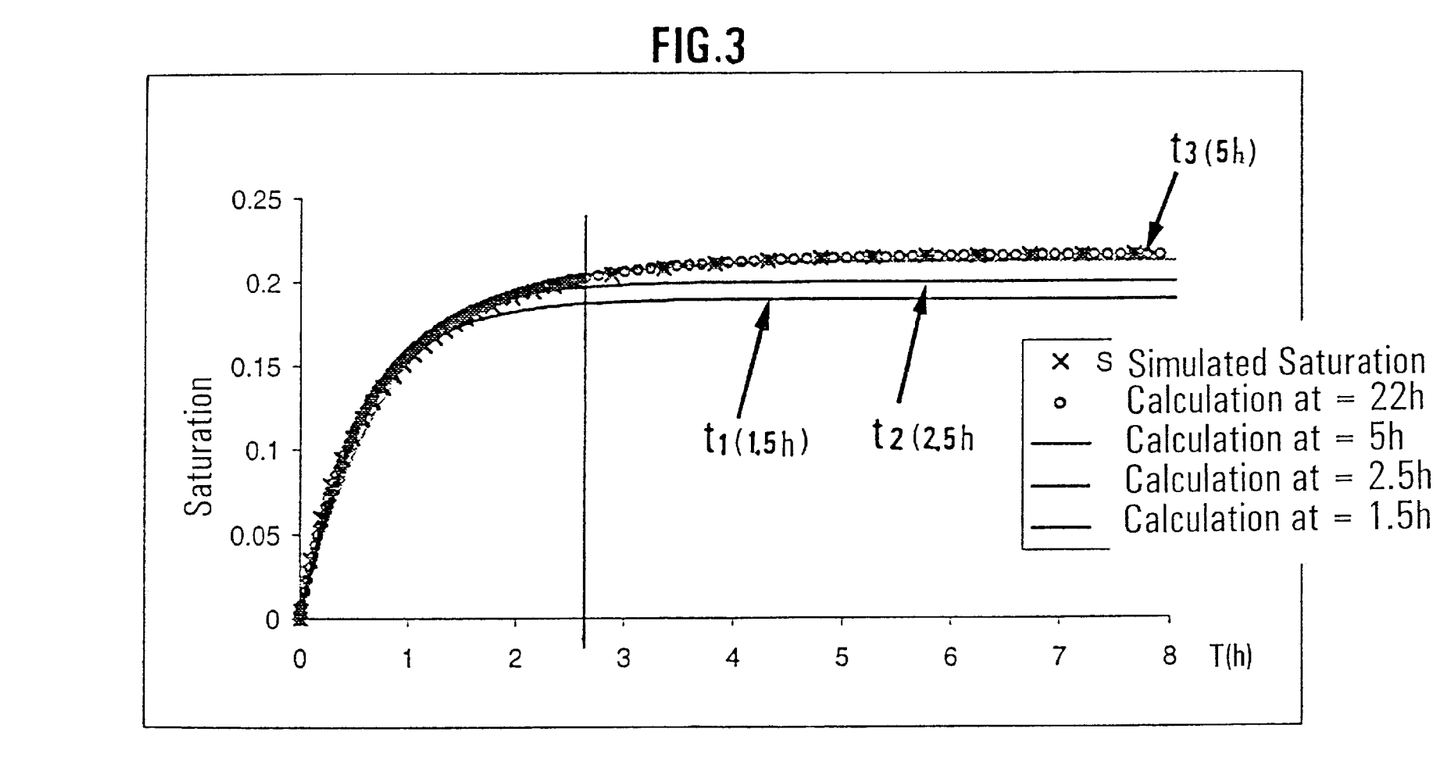
FIG. 3 shows, by way of comparison, various modelling curves obtained at different times of the same speed stage.

At each new rotating speed stage, the control device performs a new measurement acquisition and a new pair of data is obtained (time, production). The program then adjusts the bi-exponential mathematical modelling to the points curve already available (FIG. 3). The evolution of time constant T2 is thus obtained, which determines the stabilization and final saturation $S_{final}$ with time. In this program, a maximum difference is fixed between two consecutive values of T2 and $S_{final}$, corresponding for example to the practical precision of the measuring device. When the calculated differences are below these values, it may be assumed that T2 and $S_{final}$ are sufficiently stabilized and therefore that the production curve is entirely determined, and the next speed stage can be dealt with.

Figure 4A:
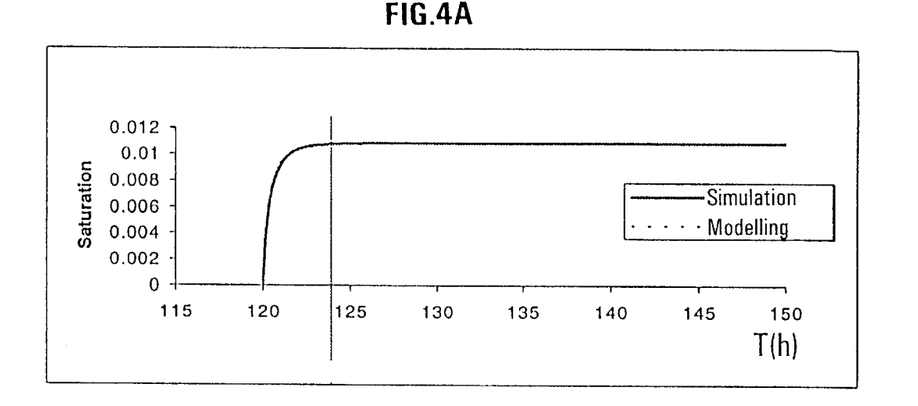
FIGS. 4a, 4b and 4c show the compared evolutions respectively of a production curve, a variation curve of the time constant T2 involved in modelling of the simulation curve, and the variation curve of the final value $S_{final}$ that can be predicted by simulation.
Figure 4B:
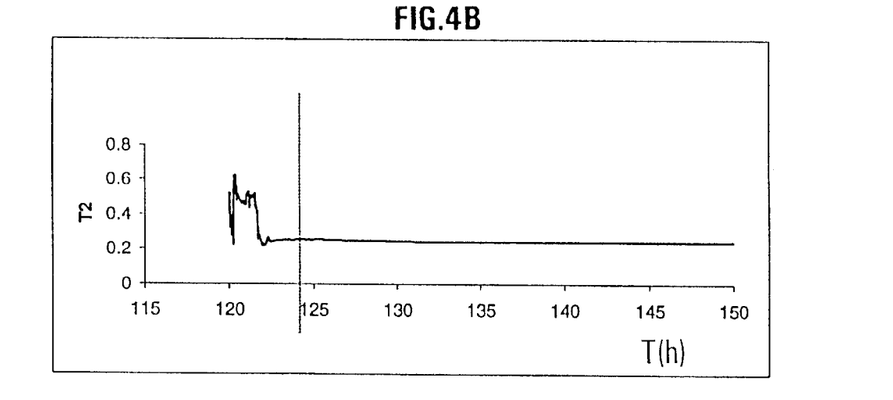
Figure 4C:
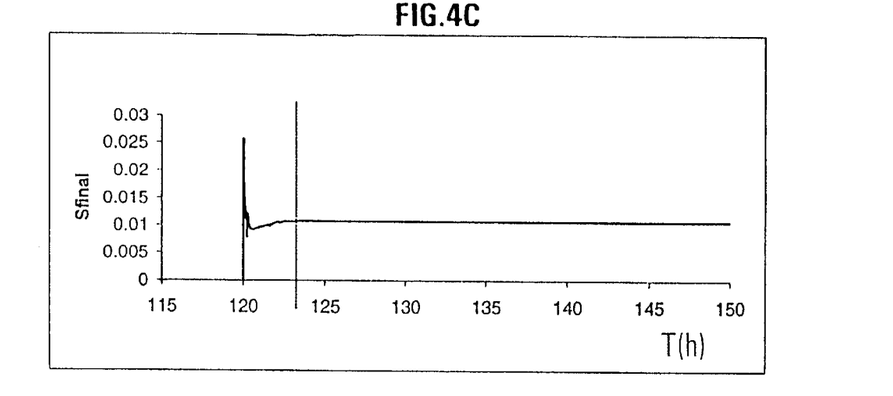

Their evolution is shown in FIGS. 4a to 4c. A very marked stabilization of time constant T2 and of the final saturation can be observed. This stabilization occurs as soon as the flow reaches the final plateau, i.e. as soon as the capillary forces become preponderant. Constant T1 stabilizes much faster since T1 only relates to the first part of the curve.

Figure 5:
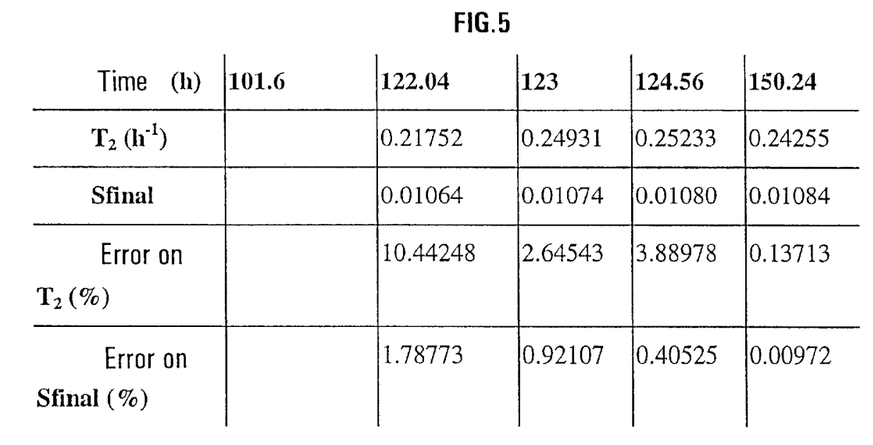
FIG. 5 is a table showing an example of compared evolutions of several parameters during the same speed stage, FIGS. 6a, 6b, 6c and 6d respectively show the evolution in time of the saturation value $S_{final}$ of a sample, of coefficients T1 and T2 used as parameters in the simulated curve and the corresponding production curve.
Figure 6A:
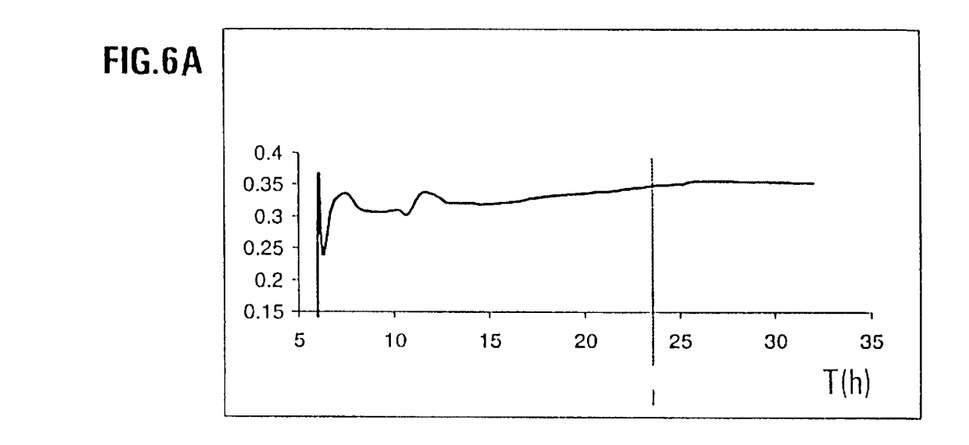
Figure 6B:
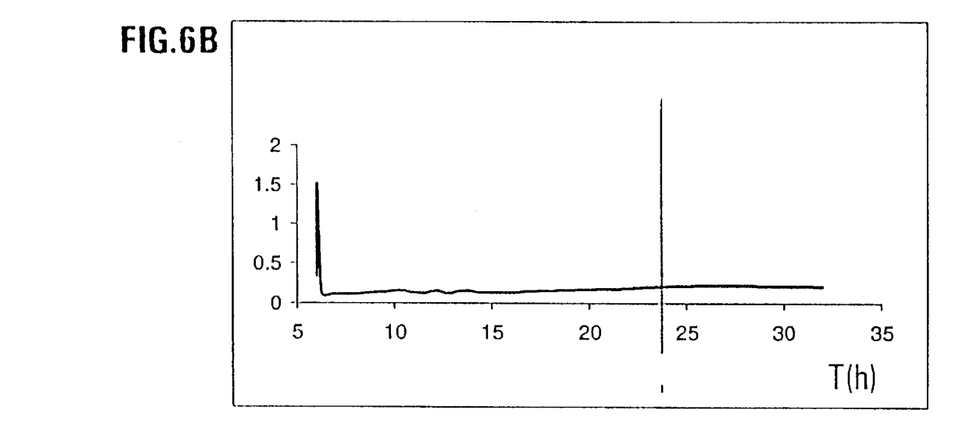
Figure 6C:
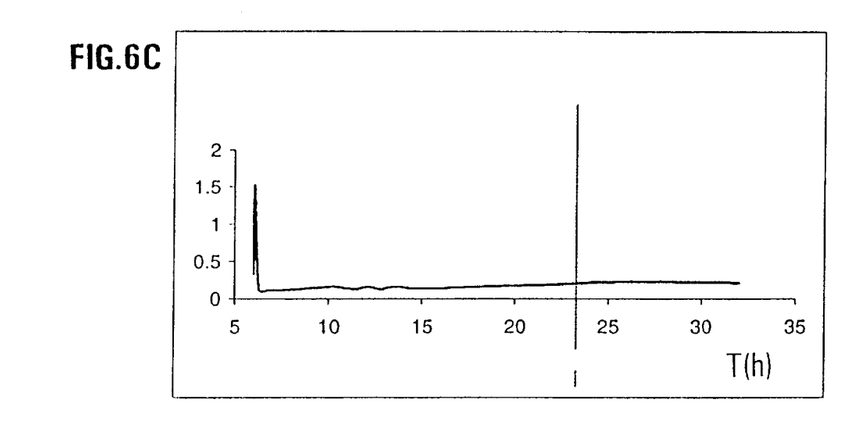
Figure 6D:
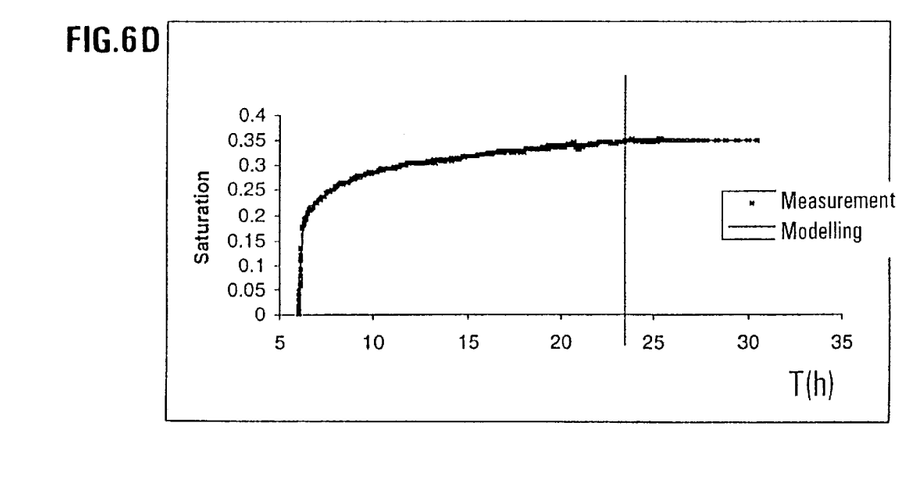

The table in FIG. 5 shows the evolution with time of four parameter sets P, T1 T2, $S_{final}$ calculated at four different times of the experiment.

If the accuracy of the capacitive sonde measuring saturation S in the vessel containing the sample is of the order of 1.5% of the pore volume for example, i.e. 1.5% in saturation, it can be considered that the final saturation value is known after a 3-hour experiment. This implies a 2.6% error on T2 and a 0.9% error on $S_{final}$, below the accuracy of the sonde. If one waited for effective stabilization of the saturation where the differences between successive measurements become smaller than the sonde accuracy, the speed stage should last about ten hours. The duration of the experiment is thus divided by three.

The peak of the stabilization observed on the simulated curves is found for parameters T2 and $S_{final}$ from an experimental curve. The evolutions shown in FIGS. 6a to 6d are obtained.

Figure 7:
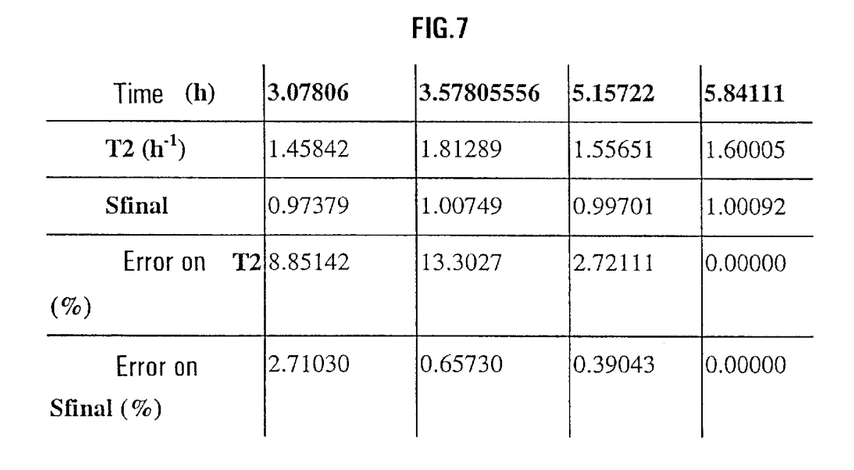
FIG. 7 is a table showing a second example of compared evolution of several parameters during the same speed stage, FIG. 8a diagrammatically shows a saturation variation curve Sw and FIGS. 8b and 8c respectively show graphs connecting various coefficients and which correspond to two saturation variation zones.

The table in FIG. 7 shows similar results for another experimental case.

After 3.5 hours, the final saturation value is known to 0.66%, which is less than the measuring accuracy. If one had waited for stabilization, the experiment would have lasted for more than 7 hours. The duration of the test can thus be reduced by half, by a factor of the order of 2 or 3. It can thus be considered that, considering these two examples, when the value of T2 is stable to 5% and the value of $S_{final}$ is stable to 1%, the mathematical modelling parameters are sufficiently determined to allow the experiment to be stopped and the next speed stage to be addressed.

Determination of the Relative Permeability Curves.

Corey's equation, which is well-known, is used for determining the relative permeability curves for oil and water, Kr and nr and. Kr and r respectively, from the respective saturations Snr and Sr obtained during the experiment:

$$\frac{K_{r,r}}{K^0_{r,r}} = S_r^{*n_1} \quad \text{and} \quad \frac{K_{r,nr}}{K^0_{r,nr}} = S_{nr}^{*n_2} \qquad (2)$$

when n1, n2 are coefficients.

A database is therefore formed, that can be presented in form of graphs for example, allowing connection of the coefficients of constant T2 to exponents n1 and n2, for different values of these exponents. A sample of determined length (6 cm for example) and with a given permeability (100 mD for example) is considered, and coefficients n1 and n2 are varied between 1 and 5 each.

Figure 8A:
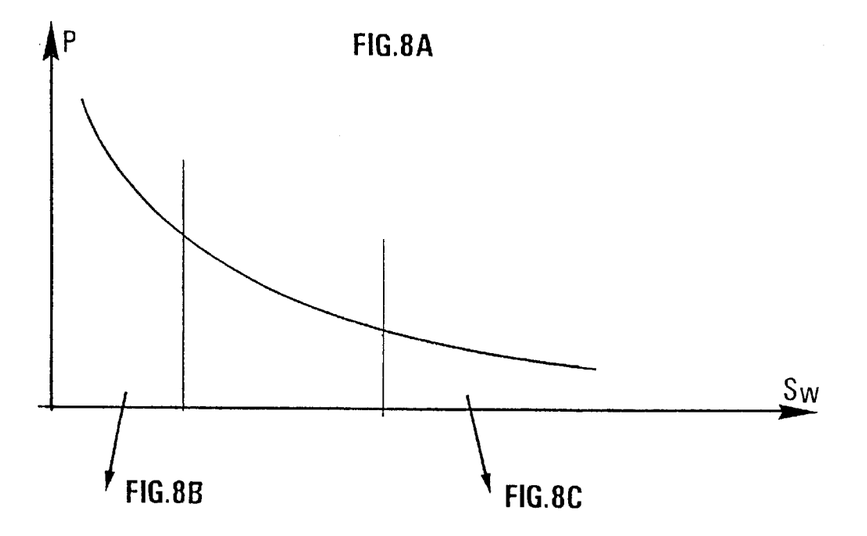
Figure 8B:
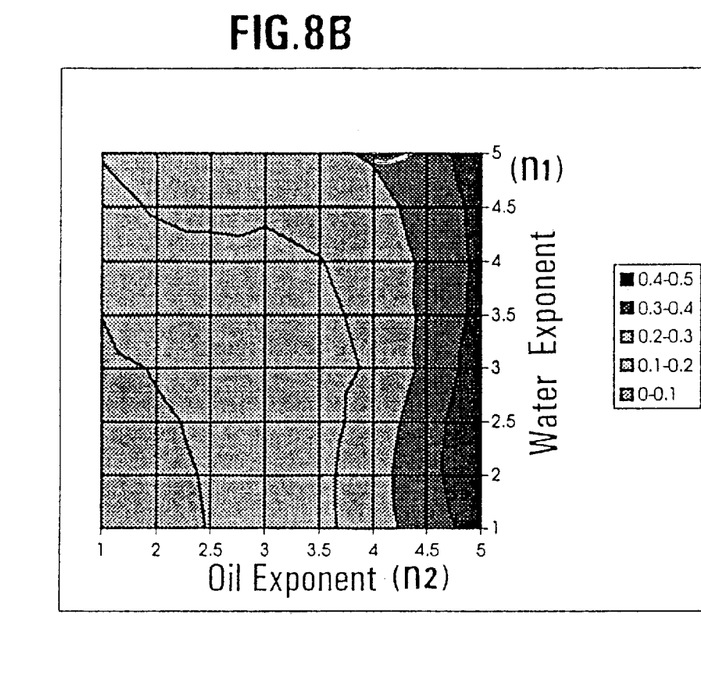
Figure 8C:
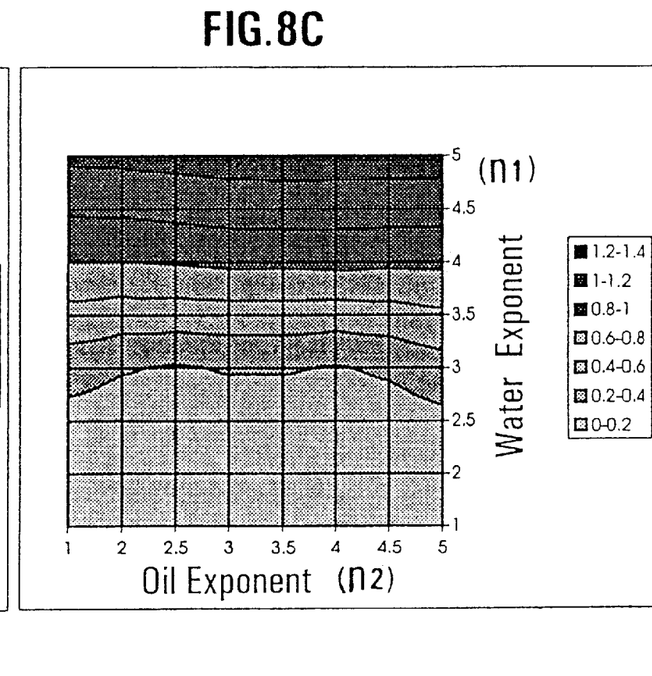

Production curves S(t) are determined for various speed stages by means of the simulator. As mentioned above, the values of P, T1 and T2 allowing best adjustment of the modelled curve to the saturation curve variation are determined by applying relation 1. For all the value triplets (T1, n1 and n2), value charts are formed or, more practically, graphs such as those shown in FIGS. 8a and 8b, corresponding to different stages of each saturation curve (FIG. 8c).

For a speed stage V1 corresponding to a high water saturation Sw, it can be actually observed that exponent n2 for oil has a predominant influence. The greater it is, i.e. the more the oil relative permeability is curved, the greater time constant T2. It can however be noted that, for this stage, the water exponent also plays a part, even though it is less marked.

For speed stage V3 corresponding to a low water saturation Sw, the predominance of exponent n1 for water is very clear. Exponent n2 for oil has no influence any longer.

For intermediate stages, it can be seen that the two exponents are by no means insignificant. At this stage, the flow is sensitive to the low relative permeability to each fluid.

The tables or graphs formed can be used for samples of different lengths and permeabilities, certain corrective factors being then applied.

Using short samples allows to reduce the duration of a production stage. However, using a longer sample allows to spread the transient parts over the curves and thus to optimize determination of the relative permeabilities. It is observed that, for samples of the same rock but of different lengths, a second degree polynomial type relation can be drawn between the stabilization time and the length. To go from a sample of length L1 (the sample used for drawing the graphs) to a sample of different length L2, the following relation can be applied:

$$\frac{T_2(L_2)}{T_2(L_1)} = \left(\frac{L_2}{L_1}\right)^2$$

A quasi-linear evolution of time constants T1 and T2 is observed as a function of the absolute permeability of the sample. A corrective factor is therefore applied:

$$\frac{T_2(K_2)}{T_2(K_1)} = \left(\frac{K_2}{K_1}\right)$$

Validation of the Method

Figure 9:
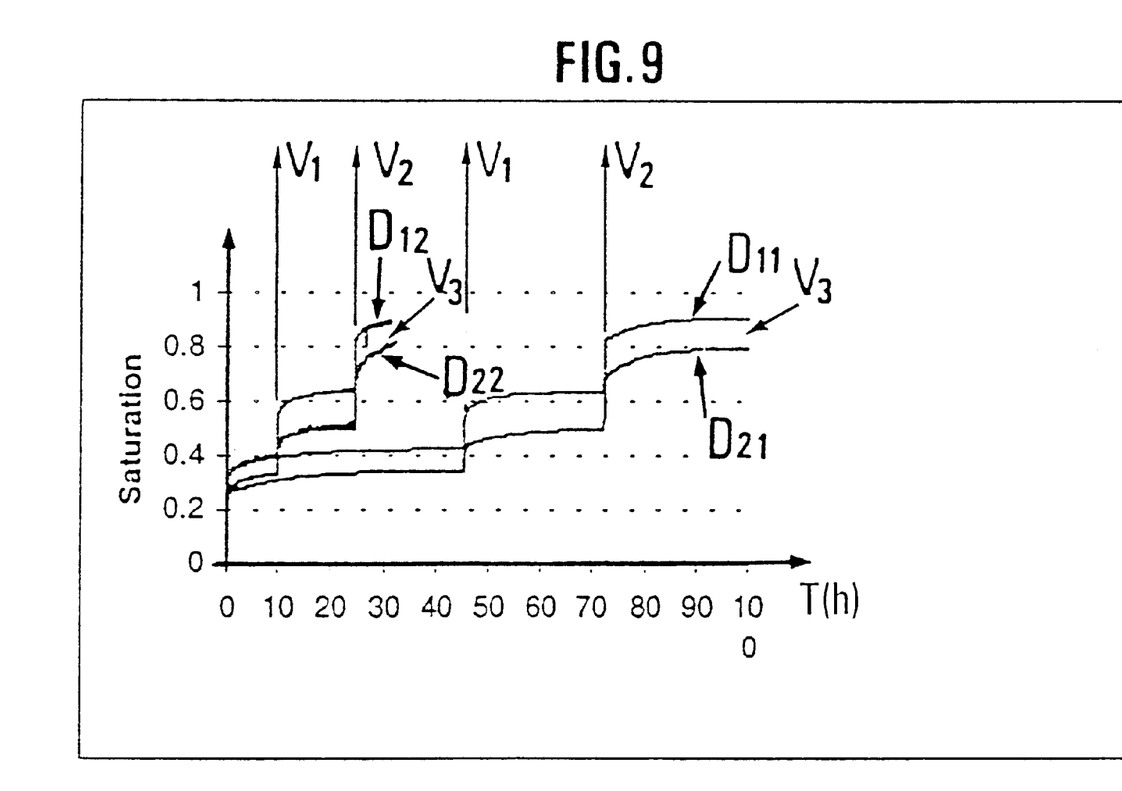
FIG. 9 shows the compared evolutions of saturation curves obtained according to the conventional method (D11 and D21) and according to the fast method according to the invention (D12 and D22)

Two samples were centrifuged, the first one water wet, the second one rather oil wet, a first time according to the conventional method, the second time according to the method described. 3 successive speed stages were applied: 470, 600 and 1050 rpm, determined after simulation tests, and the production curves shown in FIGS. 9a and 9b were obtained.

Figure 10:
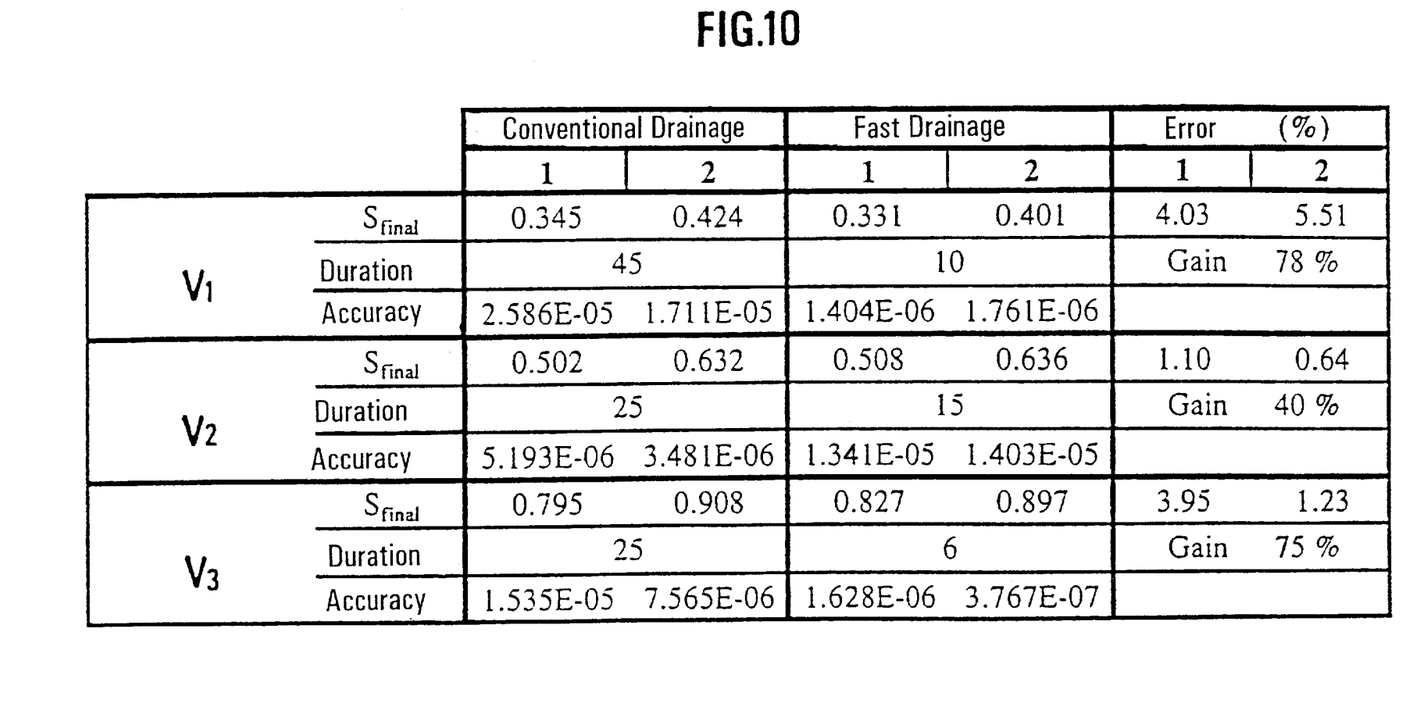
FIG. 10 is a comparative table of numerical values for three speed stages, according to whether the conventional method or the accelerated method according to the invention is used, and FIG. 11 diagrammatically shows the organization of a flow simulator.

Concerning equilibrium saturations, the results obtained are given in the table of FIG. 10.

It can be noted that the final saturation accuracy greatly depends on the duration of the stage.

The fast drainage for stages 1 and 3 thus leads to a final saturation that is slightly different from the effective stabilization. However, the duration of these two stages is greatly reduced. Stage 3 on the other hand gives quite satisfactory results, but its duration is much less reduced.

There is thus a compromise between measuring accuracy and duration. After different tests, it is suggested to fix the variation criteria of parameters T2 and $S_{final}$ to 2% and 0.5% respectively. However, these values should be estimated according to each case. In fact, it can be noted that there are samples for which time constant T2 is difficult to stabilize when the final saturation is already well-determined.

Furthermore, the fact of not waiting for stabilization of the fluids before proceeding to a new stage does not disturb the shape of the production curve. In fact, a biexponential modelling can always be associated therewith. The precision of the modelling adjustment to the experimental curves remains very acceptable (of the order of $10^{-5}$).

A modelling type involving exponential functions has been described. Other types of functions (spines for example) that can be connected to significant physical parameters of the sample could however be used without departing from the scope of the invention.

What is claimed is:

1. A method for determining physical parameters relating to circulation of fluids through a porous geologic sample comprising:
    a) placing in a vessel the sample initially saturating with a first fluid;
    b) centrifuging the sample in presence of a second fluid at rotating speeds varying progressively in stages;
    c) measuring at each rotating speed an amount of the first and second fluid progressively displaced by the centrifugation and deducing thereof variation with respect to time a saturation curve for each rotating speed;
    d) determining by selecting adjustment parameters at each rotating speed a modeling saturation curve best fitting a measured portion of the saturation curve already measured and deducing therefrom an asymptotic saturation value; and e) at each rotating speed extending the measured portion of the saturation curve already measured vs. time until the symptotic saturation is stabilized so as to obtain stabilized asymptotic saturation values for all the rotation speeds and determining therefrom the physical parameters.

2. A method as claimed in claim 1, comprising:

modelling the saturation curve by a sum of exponential functions depending on adjustment parameters.

3. A method as claimed in claim 1, comprising:

selecting centrifugation speeds which produce an even distribution of data points on the saturation curve for each rotating speed.

4. A method in accordance with claim 3 wherein the parameters comprise:

at least one of $S_{eq}$ with $S_{eq}$ being saturation at equilibrium, P with P being a weight fact, and $T_1$ and $T_2$ with $T_1$ and $T_1$ being time constants.

5. A method in accordance with claim 2 wherein the parameters comprise:

at least one of $S_{eq}$ with $S_{eq}$ being saturation at equilibrium, P with P being a weight fact, and $T_1$ and $T_2$ with $T_1$ and $T_1$ being time constants.

6. A method in accordance with claim 3 wherein the parameters comprise:

at least one of $S_{eq}$ with $S_{eq}$ being saturation at equilibrium, P with P being a weight fact, and $T_1$ and $T_2$ with $T_1$ and $T_1$ being time constants.

7. A method as claimed in claim 1, wherein modelling each saturation curve comprises:

using a flow simulator for modelling a relation between values of relative permeability respectively for the first fluid and the second fluid of a sample of determined volume and permeability, and values of saturation obtained with the first and second fluids according to coefficients and establishing a database connecting adjustment parameters to the coefficients, for saturation values relative to at least one of the first and second fluids; and determining the relative permeabilities of the sample subjected to centrifugation with reference to corresponding values extracted from the database.

8. A method as claimed in claim 2, wherein modelling each saturation curve comprises:

using a flow simulator for modelling a relation between values of relative permeability respectively for the first fluid and the second fluid of a sample of determined volume and permeability, and values of saturation obtained with the first and second fluids according to coefficients and establishing a database connecting adjustment parameters to the coefficients, for saturation values relative to at least one of the first and second fluids; and determining the relative permeabilities of the sample subjected to centrifugation with reference to corresponding values extracted from the database.

9. A method as claimed in claim 3, wherein modelling each saturation curve comprises:

using a flow simulator for modelling a relation between values of relative permeability respectively for the first fluid and the second fluid of a sample of determined volume and permeability, and values of saturation obtained with the first and second fluids according to coefficients and establishing a database connecting adjustment parameters to the coefficients, for saturation values relative to at least one of the first and second fluids; and determining the relative permeabilities (K) of the sample subjected to centrifugation with reference to corresponding values extracted from the database.

10. A method as claimed in claim 4, wherein modelling each saturation curve comprises:

using a flow simulator for modelling a relation between values of relative permeability respectively for the first fluid and the second fluid of a sample of determined volume and permeability, and values of saturation obtained with the first and second fluids according to coefficients and establishing a database connecting adjustment parameters to the coefficients, for saturation values relative to at least one of the first and second fluids; and determining the relative permeabilities of the sample subjected to centrifugation with reference to corresponding values extracted from the database.

11. A method as claimed in claim 5, wherein modelling each saturation curve comprises:

using a flow simulator for modelling a relation between values of relative permeability respectively for the first fluid and the second fluid of a sample of determined volume and permeability, and values of saturation obtained with the first and second fluids according to coefficients and establishing a database connecting adjustment parameters to the coefficients, for saturation values relative to at least one of the first and second fluids; and determining the relative permeabilities of the sample subjected to centrifugation with reference to corresponding values extracted from the database.

12. A method as claimed in claim 6, wherein modelling each saturation curve comprises:

using a flow simulator for modelling a relation between values of relative permeability respectively for the first fluid and the second fluid of a sample of determined volume,and permeability, and values of saturation obtained with the first and second fluids according to coefficients and establishing a database connecting adjustment parameters to the coefficients, for saturation values relative to at least one of the first and second fluids; and determining the relative permeabilities of the sample subjected to centrifugation with reference to corresponding values extracted from the database.

13. A method in accordance with claim 7 wherein:

the coefficients are a pair of exponents.

14. A method in accordance with claim 8 wherein:

the coefficients are a pair of exponents.

15. A method in accordance with claim 9 wherein:

the coefficients are a pair of exponents.

16. A method in accordance with claim 10 wherein:

the coefficients are a pair of exponents.

17. A method in accordance with claim 11 wherein:

the coefficients are a pair of exponents.

18. A method in accordance with claim 12 wherein:

the coefficients are a pair of exponents.

\* \* \* \* \*